US006496585B1

(12) United States Patent
Margolis

(10) Patent No.: US 6,496,585 B1
(45) Date of Patent: Dec. 17, 2002

(54) ADAPTIVE APPARATUS AND METHOD FOR TESTING AUDITORY SENSITIVITY

(76) Inventor: Robert H. Margolis, 4410 Dellwood St., Arden Hills, MN (US) 55112

( * ) Notice: Subject to any disclaimer, the term of this patent is extended or adjusted under 35 U.S.C. 154(b) by 0 days.

(21) Appl. No.: 09/491,924

(22) Filed: Jan. 27, 2000

Related U.S. Application Data

(60) Provisional application No. 60/117,402, filed on Jan. 27, 1999.

(51) Int. Cl.[7] ............................ H04R 29/00; A61B 5/00
(52) U.S. Cl. ........................................... 381/60; 600/559
(58) Field of Search .............................. 381/60; 600/559

(56) References Cited

U.S. PATENT DOCUMENTS

| | | | | |
|---|---|---|---|---|
| 4,862,505 A | * | 8/1989 | Keith et al. | 381/600 |
| 5,197,332 A | * | 3/1993 | Shennib | 600/559 |
| 5,811,681 A | * | 9/1998 | Braun et al. | 600/559 |
| 5,833,626 A | * | 11/1998 | Leysieffer | 600/559 |
| 6,167,138 A | * | 12/2000 | Shennib | 381/60 |

OTHER PUBLICATIONS

"Methods for Manual Pure–Tone Threshold Audiometry", *American National Standard, ANSI S3.21–1978 (ASA 19–1978)*, Published by the American Institute for Physics for the Acoustical Society of America, pp. 1–7, 10, (1978).

Carhart, R., et al., "Preferred Method For Clinical Determination Of Pure–Tone Thresholds", *Journal of Speech and Hearing Disorders*, 24 (4), pp. 330–345, (Feb. 1959).

Hughson, W., et al., "Manual for Program Outline for Rehabilitation of Aural Casualties Both Military and Civilian", *Supplement to the Transactions of the American Academy of Opthalmology and Otolaryngology*, pp. 3–15, (Jan. 1944).

\* cited by examiner

Primary Examiner—Forester W. Isen
Assistant Examiner—Laura A. Grier
(74) Attorney, Agent, or Firm—Kinney & Lange, P.A.

(57) ABSTRACT

A method of testing hearing automatically selects test ear and test frequencies to produce a diagnostic audiogram providing a plurality of quantitative, examiner-independent measures of test reliability. The method automatically presents appropriate masking noise to a non-test ear. In addition, the method alerts an examiner to thresholds that may be inaccurate due to inappropriate masking or subject inconsistency. A software driven system automatically carries out the method on a test subject.

35 Claims, 4 Drawing Sheets ural casualties both military and civilians. Trans. Am. Acad. Ophthalmol. Otolaryngol. Suppl. 48, 1–15, 1944; Carhart R, Jerger J F: Preferred method for clinical determination of puretone thresholds. J.Speech Hear. Dis. 24:330–345, 1959, and later incorporated into a national standard. American National Standards Institute. American National Standard Methods for Manual Pure Tone Audiometry, ANSI S3,21–1978. However many aspects of the procedure are not standardized, such as the number of test stimuli, the temporal characteristics of the stimuli, and the rules for the use of contralateral masking noise.

Test results are influenced by a number of uncontrolled procedural and listener factors including the following.

The experience of the examiner

Shortcuts and methodologic biases of the examiner

Intraexaminer procedural variations

Interexaminer procedural variations

Previous experience of the listener

Listener response criterion

As a result of less than ideal methodologic control, the accuracy and test-retest reliability are compromised to an unknown extent. This limits the ability to compare test results across examiners and listeners as well as the ability to track changes in hearing sensitivity.

SUMMARY OF THE INVENTION

The present invention provides an Adaptive Method for Testing Auditory Sensitivity (AMTAS) wherein sensitivity of the auditory system is measured in a manner to reduce the problems associated with routine clinical hearing testing. The present invention, which may be used to replace clinical puretone audiometry in the diagnostic hearing evaluation, selects test ear and test frequency, provides contralateral masking when appropriate, and quantitatively assesses test reliability.

DETAILED DESCRIPTION

Figure 1:
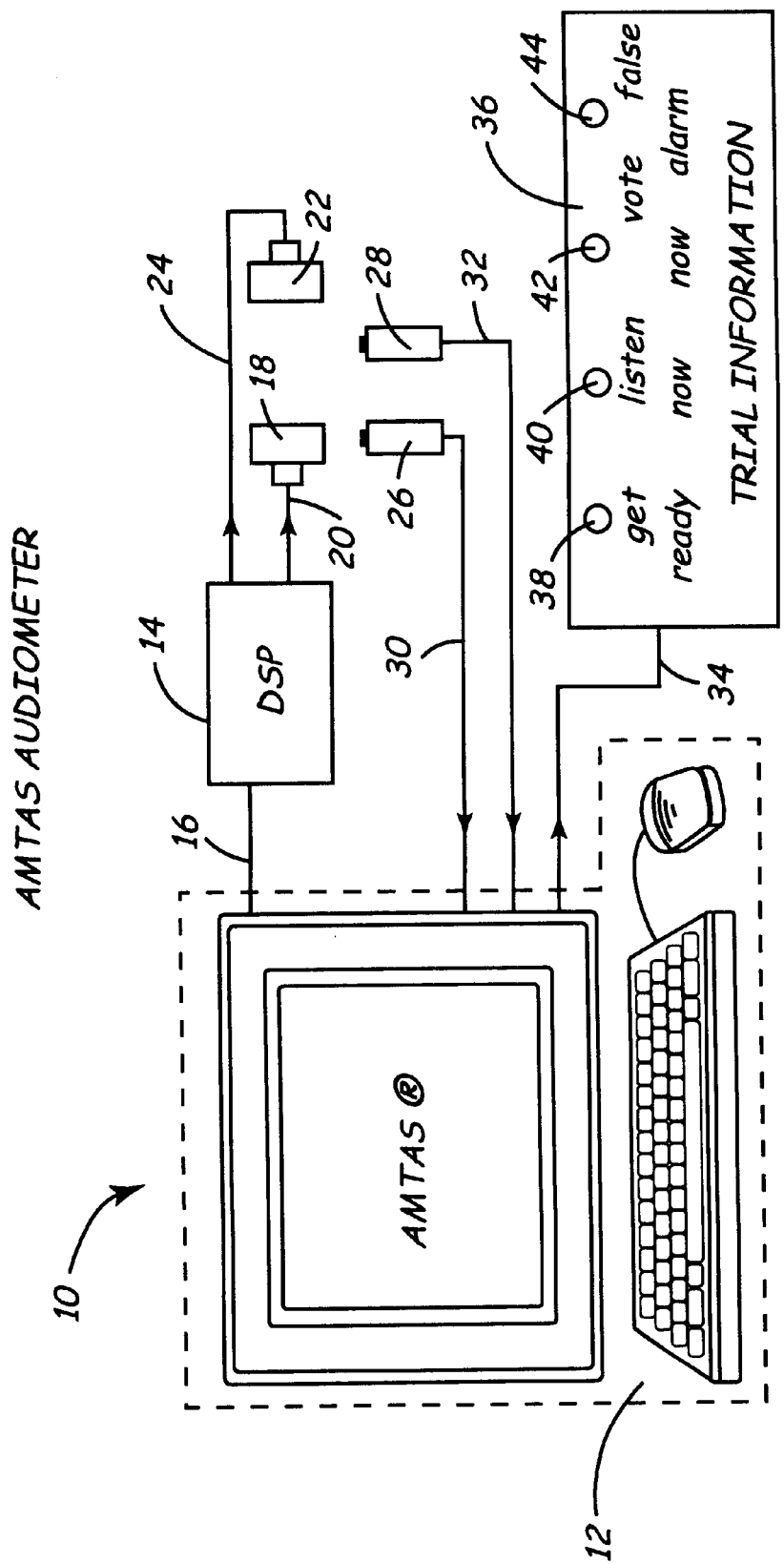
FIG. 1 illustrates an example embodiment of the AMTAS system according to the invention.

Table 1 lists definitions of terms and symbols used throughout the specification.

TABLE 1

Definition of Terms

| TERM (Default Value) | Symbol | DEFINITION |
|---|---|---|
| Subject | S | The person being tested |
| Examiner | E | The person administering the test |
| Trial | | A sequence of temporal intervals corresponding to one stimulus presentation |
| Ready Interval | $I_r$ | The first temporal interval of a trial; the interval preceding the stimulus; $I_r$ has a duration $d_r$ |
| Observation Interval | $I_o$ | The temporal interval following the Ready Interval; the interval in which the stimulus is presented; $I_o$ has a duration $d_o$ |
| Vote Interval | $I_v$ | The temporal interval following the Observation Interval; $I_v$ begins at the offset of $I_o$ and ends when the subject responds |
| Level | L | The level of a stimulus; for auditory stimuli L may be specified sound pressure level or hearing level |
| Inital Level (40 dB HL) | $L_i$ | L of the first stimulus presentation in a threshold determination |
| Inital Increment (10 dB) | $\Delta L_i$ | the amount that L is incremented when a "No" response occurs to $L_i$ |
| Stimulus Decrement (10 dB) | $\Delta L_d$ | The amount that L is decremented following a "yes" response |
| Stimulus Increment (5 dB) | $\Delta L_-$ | The amount that L is incremented following "No" responses that occur after the first "Yes" response |
| Maximum Level | $L_m$ | The maximum value of L for a specified stimulus |
| Criterion Level | $L_c$ | L corresponding to a "Yes" response immediately preceded by a "No" response |
| Threshold Criterion (2) | C | Number of times $L_c$ must occur at a given L to meet the definition of threshold level $L_t$ |
| Threshold Level | $L_t$ | L corresponding to threshold; L at which $L_c$ occurs C times |
| Number of Stimuli | $N_s$ | Number of stimulus presentations requires to determine $L_t$ |
| Masking Criterion | M | In the masking mode, minimum L for which masking is |

TABLE 1-continued

Definition of Terms

| TERM (Default Value) | Symbol | DEFINITION |
|---|---|---|
| [See Table 3] | | presented to the non-test ear |
| Interaural Attenuation | IA | The estimated difference in stimulus level in the test ear and non-test ear |
| [See Table 3] | | |
| Masker Level | ML | The level of the masking noise (in effective masking level) presented to teh non-test ear |
| Masker Level at Threshold | $ML_t$ | The level of the masking noise (in effective masking level) presented to the non-test ear when the test signal level is $L_t$ |
| Test-Retest Difference @ kHz or 0.5 kHz | $\Delta T_{1k}$ or $\Delta T_{0.5k}$ | Difference $L_t$ for two 1-kHz or 0.5 kHz threshold measures |
| Catch Trial | | A trial for which the observation interval contains no stimulus |
| Catch Trial Probability (20%) | $P_c$ | The probability that a trial will be a catch trial |
| False Response Probability | $P_y$ | Proportion of "Yes" responses in Catch Trials; determined for each test stimulus |
| Feedback | | Information provided to S indicating that a "Yes" vote occurred during a catch trial |
| Octave Threshold Difference Criterion | D | Difference between adjacent octave frequencies above which the interovtave frequency is tested. |

FIG. 1 is the preferred embodiment of AMTAS system 10. System 10 includes computer 12 connected to digital signal processor (DSP) 14 via line 16, transducer 18 connected to DSP 14 via line 20, transducer 22 connected to DSP 14 via line 24, yes button 26 and no button 28 are connected to computer 12 through line 30 and line 32, respectively, and line 34 connects panel 36 to computer 12. Panel 36 further includes get ready light 38, listen now light 40, vote now light 42, and false alarm light 44.

In operation, an examiner (E) presents instructions either verbally or in writing to a subject (S) as follows:

You are going to hear some tones. Most of them will be very soft. The tone may be in either ear. When the tone occurs it will always be while the "Listen Now" light is on. When the "Vote Now" light comes on, I want you to tell me if you think there was a tone when the "Listen Now" light was on. Push the YES button if you think there was a tone. Push the NO button if you did not hear a tone. You must push the YES button or the NO button when the "Vote Now" light comes on. The "False Alarm" light will come on if you pushed the YES button when there was no tone. You may hear some noise that sounds like static. If you hear a noise, ignore it and only push the YES button if you hear a tone. Do you have any questions?

Transducers 18 and 22 are placed on or behind S's ears. Thereafter, no intervention by E is required. Software installed in computer 12 carries out S's hearing test automatically.

Threshold levels, $L_t$, are determined for each of a set of air- and/or bone-conducted auditory stimuli, which E specifies. Stimuli are puretones of varying frequency. Test frequencies are selected from those in Table 2. Frequencies shown in italics are default test frequencies.

TABLE 2

| (13) Test Frequencies (kHz) | | | | | | | | | | |
|---|---|---|---|---|---|---|---|---|---|---|
| Air[1] | 0.125 | *0.25* | *0.5* | 0.75 | *1.0* | 1.5 | *2.0* | 3.0 | *4.0* | 6.0 8.0 |
| Bone[2] | | *0.25* | *0.5* | 0.75 | *1.0* | 1.5 | *2.0* | 3.0 | *4.0* | |

Default frequencies are shown in italics.
[a]Air refers to air-conduction testing
[2]Bone refers to bone-conduction testing E may use the default set of stimuli or another set of stimuli that E has selected from the frequencies in Table 2. The default set includes audiometric frequencies that are required for a diagnostic hearing evaluation and additional frequencies are automatically tested when needed.

Figure 2:
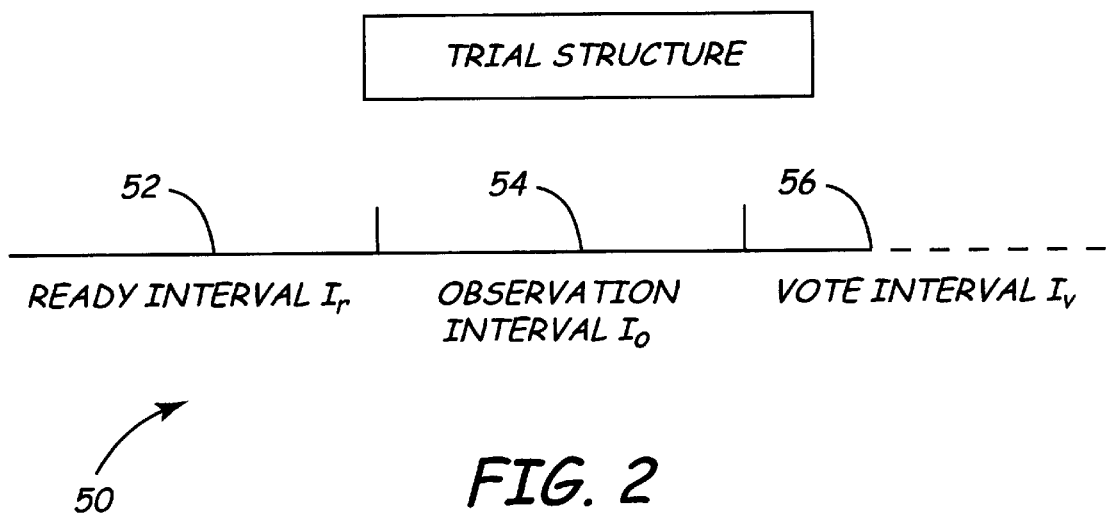
FIGS. 2 and 3 illustrate example embodiments of the methodology of the invention.

Each stimulus is presented in a trial, which is illustrated in FIG. 2. Trial structure 50 consists of Ready Interval ($I_r$) 52 of duration $d_r$, Observation Interval ($I_o$) 54 of duration $d_o$, followed by Vote Interval ($I_v$) 56 of variable duration.

The testing is performed using a psychophysical method, which is an adaptive Yes/No procedure. The stimulus is presented during $I_o$ 54. S responds during $I_v$ 56 by pushing Yes Button 18 if a stimulus was detected during $I_o$ 54 or No Button 22 if no stimulus was detected in $I_o$ 54. $I_v$ 56 ends when S responds. Catch trials, trials in which no stimulus is presented in $I_o$, are performed randomly with a predetermined probability, $P_c$, to determine S's reliability. Feedback is used to inform S when a "Yes" response occurred during a catch trial. False Alarm light 44 lights when S presses Yes button 26 during each catch trial.

The rate of stimulus presentation is determined by S's response time, allowing S to control the pace of the test. This permits testing of subjects with a wide range of age, cognitive ability, reaction time, and motor dexterity. Trials are presented repetitively at various stimulus levels L until $L_t$ is determined. The process is repeated for all E-specified stimuli or the default stimulus set.

Figure 3:
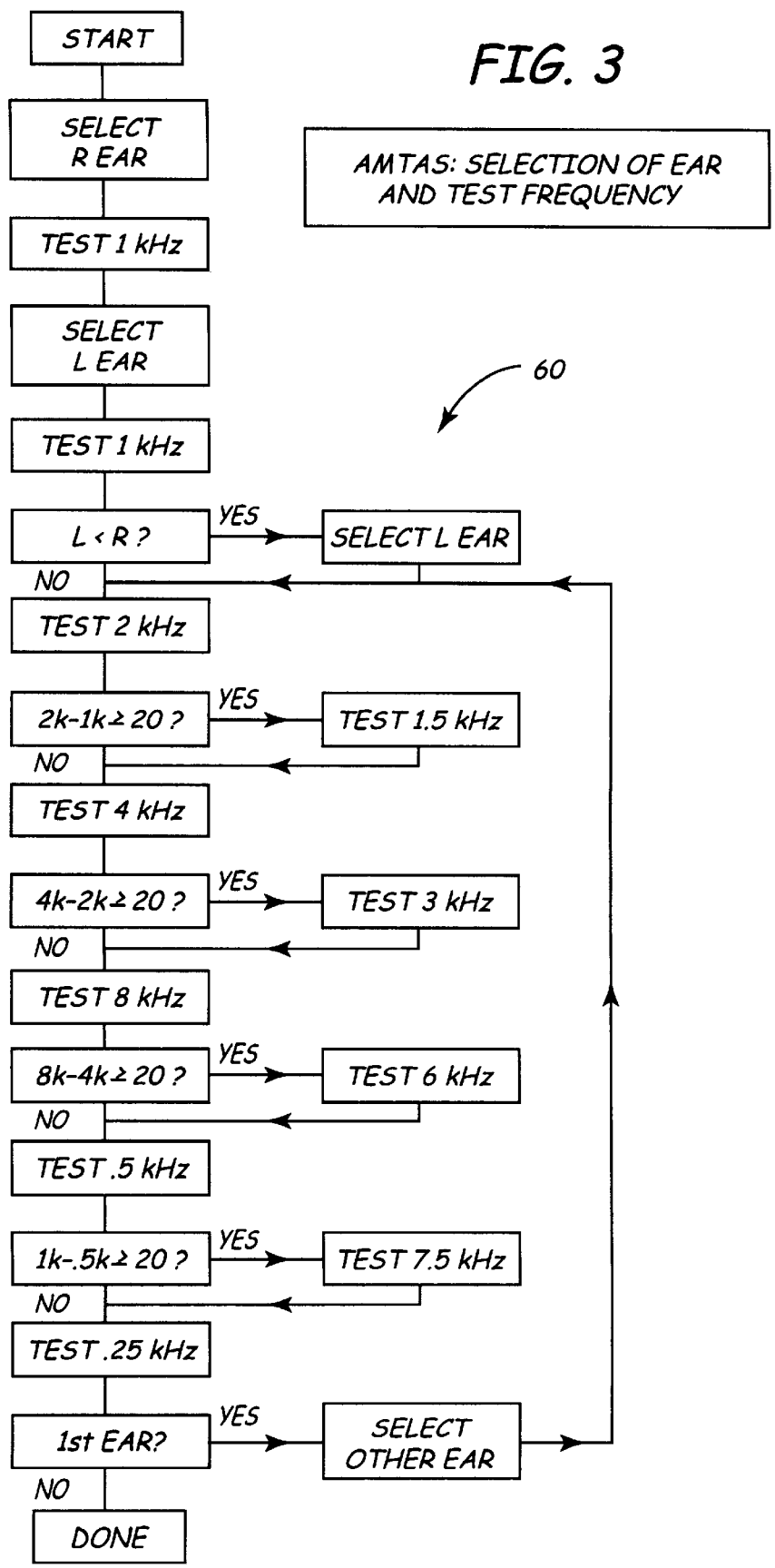

FIG. 3, consisting of flowchart 60, illustrates the logic for the selection of test frequency and test ear for air-conduction testing using the default stimulus set. The default initial test ear for air-conduction testing is the right ear. $L_t$ at 1 kHz is determined for the right ear and then for the left ear. The test ear for subsequent stimuli is the ear with the better $L_t$ at 1 kHz. For air-conduction testing, the default order of test frequencies is the following: 1 kHz, 2 kHz, 4 kHz, 8 kHz, 0.5 kHz, and 0.25 kHz. Interoctave frequencies (0.75 kHz, 1.5 kHz, 3 kHz, and 6 kHz) are automatically tested when the difference between two adjacent octave frequencies exceeds D, where D is a predetermined value. The default value of D is 20 decibels (dB). After $L_t$ is determined for all frequencies, the test is repeated at 1 kHz unless $L_t>L_m$, where $L_m$ is the maximum value of L for a specified stimulus, in which case 0.5 kHz is retested. The difference in the two 1 kHz thresholds, $\Delta T_{1k}$ (or 0.5 kHz, $\Delta T_{0.5k}$), is a measure of test reliability. After thresholds are tested for each selected frequency, the other ear is tested.

After air-conduction testing is completed, E is prompted to place the bone-conduction transducer behind the ear with the poorer $L_t$ at 1 kHz (or 0.5 kHz). An earphone is placed over the non-test ear for masking, which is explained below. If the default bone-conduction stimulus set is selected, the frequencies are tested in the following order: 1 kHz, 2 kHz, 4 kHz, 0.5 kHz, and 0.25 kHz. After all frequencies are tested, E is prompted to reverse the transducer and the other ear is tested.

When the test signal may be audible in the non-test ear, a masking signal is automatically presented to ensure that perception of the test signal by the non-test ear does not affect the test. When testing with air-conducted stimuli, masking is presented to the non-test ear in $I_o$ when L>M, where M is the masking criterion. M is the level at which the stimulus may be audible in the non-test ear of a normal hearing subject for a given stimulus/transducer combination. The masking level, ML (in effective masking level), presented to the contralateral ear is L−IA+10 dB where IA is the average interaural attenuation. M and IA are dependent on the stimulus and the transducer. The M and IA values in Table 3 may be used for two commonly used audiometric transducers. When testing with bone-conducted stimuli, the non-test ear is always masked.

If S responds "Yes" to $L_i$, Catch trial 78 is performed to provide an indication of S's reliability. If S responds "Yes" to Catch trial 78, then False Alarm light 44 illuminates (see FIG. 1) and Catch trial 80 is performed. Regardless of S's response to Catch trial 80, testing continues. If, however, S responds "No" to Catch trial 78, testing continues without performing Catch trial 80.

When testing continues, L of the next stimulus is presented at $L-\Delta L_d$ at Decrement step 82. After each "Yes" response, Catch trials 78 and 80 are performed again, and L is subsequently decremented by $\Delta L_d$. If S responds "No" at Decrement step 82, Catch trials 84 and 86 are performed as described above for Catch trials 78 and 80. For each "No" response after the first "Yes" response at Decrement step 82, L is incremented by $\Delta L_u$, which is shown at Increment step 88.

L that produces a "Yes" response immediately preceded by a "No" response is designated $L_c$. When $L_c$ occurs C times at the same value of L, where C is the threshold criterion, that level is designated $L_t$. This is illustrated by C Value step 90. The default value of C is 2, but E can set C to be any value.

The number of stimulus presentations, $N_1$, required to determine $L_t$ is a quality indicator. Adaptive method 70 is repeated for each E-selected stimulus or for the default stimulus set.

The proportion of "Yes" votes following Catch trials 78, 80, 84, and 86, designated $P_y$, is a measure of response reliability. $P_y$ is determined for each $L_t$ and an average $P_y$ is reported for each ear and for both ears combined.

After determination of air- and bone-conduction thresholds, system 10 determines threshold measurements for which masking levels may not have been appropriate. These are Masking Alerts. E is prompted to retest those thresholds, and appropriate masker levels are automatically selected. Examples of Masking Alerts are given in Table 4.

TABLE 3

| | (20) Interaural Attenuation and Masking Criteria | | | | | | | | | | |
|---|---|---|---|---|---|---|---|---|---|---|---|
| Transducer | Freq (kHz): | 0.125 | 0.25 | 0.5 | 0.75 | 1.0 | 1.5 | 2.0 | 3.0 | 4.0 | 6.0 | 8.0 |
| TDH-50 | $IA^1$ | 40 | 40 | 40 | 40 | 40 | 40 | 45 | 45 | 50 | 50 | 50 |
| | M | 30 | 30 | 30 | 30 | 30 | 30 | 35 | 35 | 40 | 40 | 40 |
| ER-3A | $IA^2$ | 75 | 75 | 75 | 75 | 70 | 55 | 50 | 50 | 50 | 50 | 50 |
| | M | 65 | 65 | 65 | 65 | 60 | 45 | 40 | 40 | 40 | 40 | 40 |
| Bone Cond | IA | | 0 | 0 | 0 | 0 | 0 | 0 | 0 | 0 | | |
| | M | | 0 | 0 | 0 | 0 | 0 | 0 | 0 | 0 | | |

[1]Average IA−5dB
[2]Average IA−10dB

Figure 4:
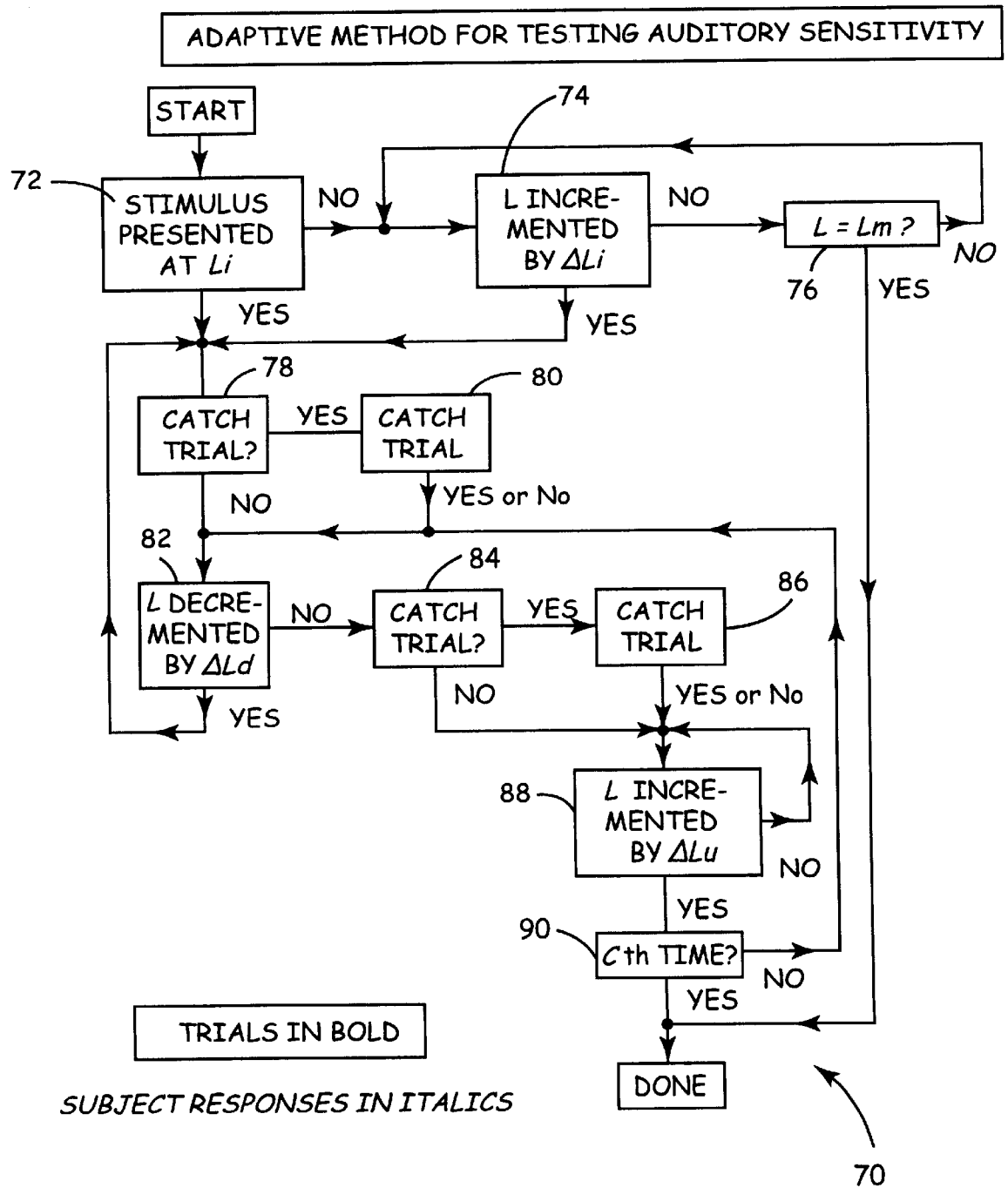
FIG. 4 is a flowchart illustrating the method of determining thresholds, $L_1$.

FIG. 4 illustrates an example embodiment of the steps in determining $L_t$ by adaptively varying L. $L_t$ is the lowest level at which S hears a tone at least 50% of the time. Adaptive method 70 of FIG. 4 includes Initial step 72, Increment step 74, Maximum Threshold step 76, Catch trials 78 and 80, Decrement step 82, Catch trials 84 and 86, Increment step 88, and C Value step 90.

In operation, the initial stimulus, $L_i$, is presented to S at Initial step 72. If S responds "No" to $L_i$, L of the next stimulus is presented at $L+\Delta L_i$ at Increment step 74. Increment step 74 is repeated by incrementing L by $\Delta L_i$ until a "Yes" response occurs or until $L=L_m$. If L reaches $L_m$ then $L_t>L_m$.

TABLE 4

| | Masking Alerts |
|---|---|
| AIR CONDUCTION | $ML_t \leq$ air conduction $L_t$ of non-tested ear |
| | $ML_t \leq$ bone conduction $L_t$ of non-tested ear |
| BONE CONDUCTION | $ML_t \leq$ air conduction, $L_t$ of non-tested ear |
| | $ML_t - IA \geq$ bone conduction $L_t$ of test ear |

Results are presented in standard audiogram format. The quality indicators listed in Table 5 are reported.

TABLE 5

Quality Indicators

| | |
|---|---|
| $P_y(f)$ | False alarm probability at each test frequency |
| $P_y(ear)$ | False alarm probability for ear. |
| $P_y(S)$ | False alarm probability for both ears combined |
| $N_t(f)$ | Number of trials required to determine $L_t$ for each frequency |
| $\Delta T_{1k}$ or $\Delta T_{0.5k}$ | Test-retest difference at 1 kHz or 0.5 kHz |

For each threshold measurement, two quality indicators are reported, $P_y$ and $N_t$. In addition, $P_y$ is reported for each ear and both ears combined. $\Delta T_{1k}$ or $\Delta T_{0.5k}$ is also reported. Values of each quality indicator that exceed two standard deviations beyond the mean are identified. $ML_t$, the masker level at threshold, is reported for each threshold and Masking Alerts are identified.

System 10 and the corresponding method for adaptively testing auditory sensitivity selects a test ear and test frequency, provides contralateral masking when appropriate, and quantitatively assesses test reliability. System 10 and the corresponding method are designed to eliminate the major sources of human error that influence the accuracy of manual puretone audiometry. A summary of the unique features of system 10 and the method contrasted with manual puretone audiometry are presented in Table 6.

TABLE 6

AMTAS Features Contrasted to Manual Puretone Audiometry

| MANUAL PURETONE AUDIOMETRY | AMTAS |
|---|---|
| Requires continous control by E | No intervention by E required |
| E selects test ear and test frequencies | Test ear and test frequencies automatically selected to produce complete diagnostic audiogram |
| Provides only qualitative assessment of test reliability which is highly dependent on E's experience | provides five quantitative, E-independent measures of test reliability |
| Requires E to determine the need for masking the non-test ear and to manually select masker levels | Automatically presents appropriate masking noise to non-test ear |
| Does not identify thresholds that are likely to be inaccurate | Alerts E to thresholds that may be inaccurate due to inappropriate masking or subject inconsistency |

Although the present invention has been described with reference to preferred embodiments, workers skilled in the art will recognize that changes may be made in form and detail without departing from the spirit and scope of the invention.

What is claimed is:

1. An automated method for obtaining a diagnostic audiogram, the method comprising:
   providing a sequence of air-conducted and bone-conducted acoustic stimuli to a subject which is adaptively varied based upon responses of the subject to the stimuli; and
   deriving from the sequence and the responses a diagnostic audiogram which includes a set of hearing threshold levels and a plurality of quality indicators for assessing validity of the threshold levels, the quality indicators including at least one of false probabilities, number of trials and test-retest differences.

2. The method of claim 1 and further comprising:
   tracking a number of presentations of stimuli required to identify the threshold levels; and
   reporting the number of presentations of stimuli required to identify the threshold levels as a quality indicator.

3. The method of claim 1 and further comprising:
   presenting, automatically, a default set of stimuli to the subject;
   adding stimuli depending on the subject's responses; and
   deleting stimuli depending on the subject's responses.

4. The method of claim 1 wherein the sequence is presented in a trial including a ready interval, an observation interval, a vote interval, and a feedback interval.

5. The method of claim 4 and further comprising:
   presenting catch trials, wherein catch trials contain no stimuli in order to evaluate validity of the subject's responses;
   providing feedback to the subject if the subject responds during the catch trial allowing the subject to alter response criteria, which increases test validity; and
   tracking incorrect responses given by the subject during the catch trials to evaluate validity of a hearing test.

6. The method of claim 1 and further comprising:
   masking a contralateral ear of the subject if it is determined to be required for preventing participation of a non-test ear.

7. The method of claim 6 wherein a level of a masking noise is adjusted to correspond with a level of the stimuli insuring that the level of the masking noise presented to the non-test ear is appropriate.

8. The method of claim 7 and further comprising:
   providing masking alerts to warn when the masking noise may not have been appropriate.

9. The method of claim 1 wherein the diagnostic audiogram includes a plurality of quality indicators and masking alerts.

10. A method of testing hearing of a subject, the method comprising:
    providing, to the subject, a sequence of acoustic stimuli;
    receiving, from the subject, responses to the sequence of acoustic stimuli;
    adaptively selecting the acoustic stimuli of the sequence based upon the subject's responses;
    identifying hearing threshold levels based on the subject's responses;
    deriving quality indicators based upon the acoustic stimuli provided and the responses received, the quality indicators including at least one of false probabilities, number of trials and test-retest differences; and
    producing a diagnostic audiogram based upon the hearing threshold levels and the quality indicators.

11. The method of claim 10 wherein a default set of stimuli is the sequence of acoustic stimuli.

12. The method of claim 10 wherein providing a sequence of acoustic stimuli is through a temporally divided trial.

13. The method of claim 10 and further comprising:
providing catch trials for evaluating the subject's responses;
providing feedback to the subject when an incorrect response is given during the catch trial; and
determining a proportion of incorrect responses given during catch trials as a measure of test validity.

14. The method of claim 10 and further comprising:
masking a contralateral ear of the subject;
adjusting a level of masking to correspond to a level of the acoustic stimuli;
providing a masking alert if the level of acoustic stimuli is not appropriate; and
reporting the masking alert with the diagnostic audiogram.

15. A method for automatically testing hearing of a subject, the method comprising:
presenting air-conducted acoustic test stimuli to the subject;
collecting responses from the subject, the responses being based on the air-conducted acoustic test stimuli;
identifying threshold levels based on the subject's responses to the air-conducted acoustic test stimuli;
presenting bone-conducted acoustic test stimuli to the subject;
collecting responses from the subject, the responses being based on the bone-conducted acoustic test stimuli;
identifying threshold levels based on the subject's responses to the bone-conducted acoustic test stimuli;
deriving a plurality of quality assurance indicators during presentation of the air-conducted and bone-conducted acoustic test stimuli, the quality assurance indicators including at least one of false probabilities, number of trials and test-retest differences; and
generating a diagnostic audiogram based upon the threshold levels and outcomes of the quality assurance indicators.

16. The method of claim 15 wherein test stimuli presented to the subject are automatically selected, and test frequencies are automatically added and deleted depending on the responses from the subject.

17. The method of claim 16 wherein the test frequencies are automatically selected from a default stimuli set.

18. The method of claim 16 wherein a set of test frequencies is preselected.

19. The method of claim 15 and further comprising:
varying test frequencies automatically to obtain threshold levels for each test frequency.

20. The method of claim 15 wherein test stimuli are presented in a temporally divided trial structure.

21. The method of claim 20 wherein the trial structure is paced according to a response time of the subject such that a timed interval is adapted by a time needed for the subject to appropriately respond.

22. The method of claim 20 and further comprising:
presenting the temporally divided trial structure without providing a test stimulus;
providing feedback to the subject indicating that a response was incorrectly given, and allowing the subject to alter response criteria in order to increase test validity; and
providing a tally of each response as an indicator of test reliability.

23. The method of claim 22 and further comprising:
masking a contralateral ear of the subject to prevent participation of a non-test ear.

24. The method of claim 23 and further comprising:
alerting, by a plurality of masking alerts, that a noise masking the contralateral ear may not have been appropriate.

25. The method of claim 24 wherein the masking alerts are reported on the diagnostic audiograms.

26. The method of claim 23 wherein a masking level presented to the contralateral ear is equal to a test frequency level minus an average interaural attenuation plus 10 decibels.

27. The method of claim 15 and further comprising:
varying, adaptively, a level of test stimuli until the subject hears a lowest test stimulus a predetermined percentage of times that the lowest test stimulus is presented to the subject.

28. The method of claim 27 wherein the level of the test stimuli is adaptively varied by a predetermined increment to determine a level that is detectable by the subject immediately followed by a level that is not detectable by the subject.

29. The method of claim 28 wherein a threshold level test stimulus is detected by the subject a predetermined number of times and wherein one of the quality assurance indicators is determined in part by how many times the threshold level test stimulus was presented to the subject in order for the subject to detect the threshold level test stimulus a predetermined percentage of times.

30. A method for automatically testing hearing of a subject, the method comprising:
presenting a plurality of tone frequencies to the subject;
identifying a first ear and a second ear of the subject based on a threshold level of a tone frequency, the first ear having a lower threshold at the first tone frequency, and the second ear having a higher threshold at the first tone frequency;
performing air-conduction tests on the subject's first ear and then second ear;
performing bone-conduction tests on each ear; and
providing quality indicators of the air-conduction tests and the bone-conduction tests, the quality indicators including at least one of false probabilities, number of trials and test-retest differences.

31. The method of claim 30 wherein performing air-conduction tests comprise:
a) presenting, sequentially, test stimuli at pre-determined frequencies to the subject's first ear;
b) receiving responses from the subject to the stimuli;
c) identifying a threshold level for each test tone frequency for the first ear based on the responses;
d) presenting, if needed, an interoctave frequency when a difference in threshold levels of two adjacent test tone frequencies exceeds a predetermined value;
e) receiving responses from the subject to stimuli presented at the interoctave frequency;
f) identifying a threshold level for the interactive frequency based on the responses;
g) repeating a first test tone frequency to determine a difference between thresholds at the first test tone frequency to indicate test reliability for the first ear; and
h) repeating steps a–g for the second ear.

32. The method of claim 31 wherein a non-test ear of the subject is masked.

33. The method of claim 32 and further comprising:

providing masking alerts for masker levels that may not have been appropriate, the masking alerts indicated when masker level thresholds are less than or equal to the threshold level of the non-test ear.

34. The method of claim 30 wherein providing quality indicators comprises:

introducing catch trials while presenting test tone frequencies, which provides an indication of test quality by tracking accumulated false positives; and alerting the subject to the false positives given during the catch trials.

35. The method of claim 30 wherein providing quality indicators includes deriving a false alarm probability at each test tone frequency, a false alarm probability for each ear, a false alarm probability for both ears combined, a count of trials required to determine the threshold level at each test tone frequency, and results of a difference determined when retesting a first tone frequency.

* * * * *

UNITED STATES PATENT AND TRADEMARK OFFICE
CERTIFICATE OF CORRECTION

| | | |
|---|---|---|
| PATENT NO. | : 6,496,585 B1 | Page 1 of 1 |
| APPLICATION NO. | : 09/491924 | |
| DATED | : December 17, 2002 | |
| INVENTOR(S) | : Robert H. Margolis | |

It is certified that error appears in the above-identified patent and that said Letters Patent is hereby corrected as shown below:

The following heading and paragraph should be inserted in column 1, line 4; immediately before the heading "BACKGROUND OF THE INVENTION":

--STATEMENT REGARDING FEDERALLY SPONSORED RESEARCH OR DEVELOPMENT

This invention was made with government support under one or more of grant no. R41 DC005110 and grant no. R42 DC005110, both awarded by the National Institute on Deafness and Other Communication Disorders, part of the National Institutes for Health. The Government has certain rights in the invention.--

Signed and Sealed this
Twelfth Day of July, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 6,496,585 B1 | Page 1 of 1 |
| APPLICATION NO. | : 09/491924 | |
| DATED | : December 17, 2002 | |
| INVENTOR(S) | : Robert H. Margolis | |

It is certified that error appears in the above-identified patent and that said Letters Patent is hereby corrected as shown below:

The following heading and paragraph should be inserted in column 1, line 4; immediately before the heading "BACKGROUND OF THE INVENTION":

--STATEMENT REGARDING FEDERALLY SPONSORED RESEARCH OR DEVELOPMENT

This invention was made with government support under one or more of grant no. R41 DC005110 and grant no. R42 DC005110, both awarded by the National Institutes of Health. The Government has certain rights in the invention.--

This certificate supersedes the Certificate of Correction issued July 12, 2011.

Signed and Sealed this
Thirteenth Day of March, 2012

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 6,496,585 B1 | Page 1 of 1 |
| APPLICATION NO. | : 09/491924 | |
| DATED | : December 17, 2002 | |
| INVENTOR(S) | : Robert H. Margolis | |

It is certified that error appears in the above-identified patent and that said Letters Patent is hereby corrected as shown below:

The following heading and paragraph should be inserted in column 1, line 4; immediately before the heading "BACKGROUND OF THE INVENTION":

--STATEMENT REGARDING FEDERALLY SPONSORED RESEARCH OR DEVELOPMENT

This invention was made with government support under grant no. R41 DC005110 and grant no. R42 DC005110, both awarded by the National Institutes of Health. The Government has certain rights in the invention.--

This certificate supersedes the Certificate of Correction issued July 12, 2011 and March 13, 2012.

Signed and Sealed this
Fifteenth Day of May, 2012

David J. Kappos
*Director of the United States Patent and Trademark Office*